United States Patent [19]

Bolduc

[11] 3,960,141
[45] June 1, 1976

[54] ELECTROSURGICAL AND ECG MONITORING SYSTEM

[76] Inventor: Lee R. Bolduc, 4624 W. 28th St., Minneapolis, Minn. 55416

[22] Filed: Mar. 6, 1975

[21] Appl. No.: 556,158

[52] U.S. Cl. .................... 128/2.06 E; 128/303.13; 128/416; 128/DIG. 4
[51] Int. Cl.² .................... A61B 5/04; A61N 3/06
[58] Field of Search ........... 128/2.06 E, 2.1 E, 2.1 P, 128/303.13, 303.14, 404, 416, 417, 418, DIG. 4, 303.17

[56] References Cited
UNITED STATES PATENTS

| | | | |
|---|---|---|---|
| 3,380,445 | 4/1968 | Frasier | 128/2.06 E |
| 3,534,727 | 10/1970 | Roman | 128/2.06 E |
| 3,543,760 | 12/1970 | Bolduc | 128/416 |
| 3,572,322 | 3/1971 | Wade | 128/2.06 E |
| 3,612,061 | 10/1971 | Collins | 128/418 |
| 3,895,635 | 7/1975 | Justus et al. | 128/303.13 |

Primary Examiner—Robert W. Michell
Assistant Examiner—Lee S. Cohen
Attorney, Agent, or Firm—Burd, Braddock & Bartz

[57] ABSTRACT

A system for simultaneously monitoring a patient's beat-by-beat heart signals during an electrosurgical operating procedure. A combined ground and pickup electrode is used as an indifference electrode and a bioelectric signal electrode. The electrode is connected to an ECG monitoring system having an electronic signal viewing screen for visually viewing the heart tracing and a recorder for making a strip chart of the patient's heart signals. The bioelectric pickup electrodes are arranged on the ground electrode in a manner to minimize interference from the use of the electrosurgical unit on the patient whereby the surgeon is provided with instantaneous information regarding the condition of the patient's heart during the electrosurgical operation.

34 Claims, 6 Drawing Figures

ELECTROSURGICAL AND ECG MONITORING SYSTEM

BACKGROUND OF INVENTION

Electrosurgical units used for cautery, fulguration and electrocoagulation utilize ground electrodes in engagement with the patient to ground the patient. An example of a ground plate electrode is disclosed by Bolduc in U.S. Pat. No. 3,543,760. Electrosurgical units utilize a high frequency current in a localized area to effect cutting and coagulation action. These high frequency signals establish interference noise signals which inhibit the monitoring of ECG signals during the electrosurgical operation. The conventional ECG recording equipment is not compatible with the electrosurgical machines. The ECG monitoring units use separate electrodes attached to the patient's extremities, as shown, for example, in U.S. Pat. No. 3,029,820.

SUMMARY OF INVENTION

The invention relates to a system for monitoring a patient's heart signals simultaneously with the operation of an electrosurgical unit. The system comprises an electrosurgical unit having an active electrode and an inactive or ground electrode adapted to make surface contact with the skin of the patient. The ground electrode is connected with a cable and clamp to the electrosurgical signal generator. A plurality of bioelectric pickup electrodes are mounted on the ground electrode and adapted to contact separate portions of the patient's body. Each bioelectric pickup electrode is surrounded by an equal surface area of the electrical conductor for the ground electrode so that interference signals from the electrosurgical procedure have a minimum of interference with the bioelectric pickup potential difference between the bioelectric pickup electrodes. An electrical insulator means is used to mount each of the bioelectric pickup electrodes on the ground electrode.

IN THE DRAWINGS

DESCRIPTION OF PREFERRED EMBODIMENT

Figure 1:
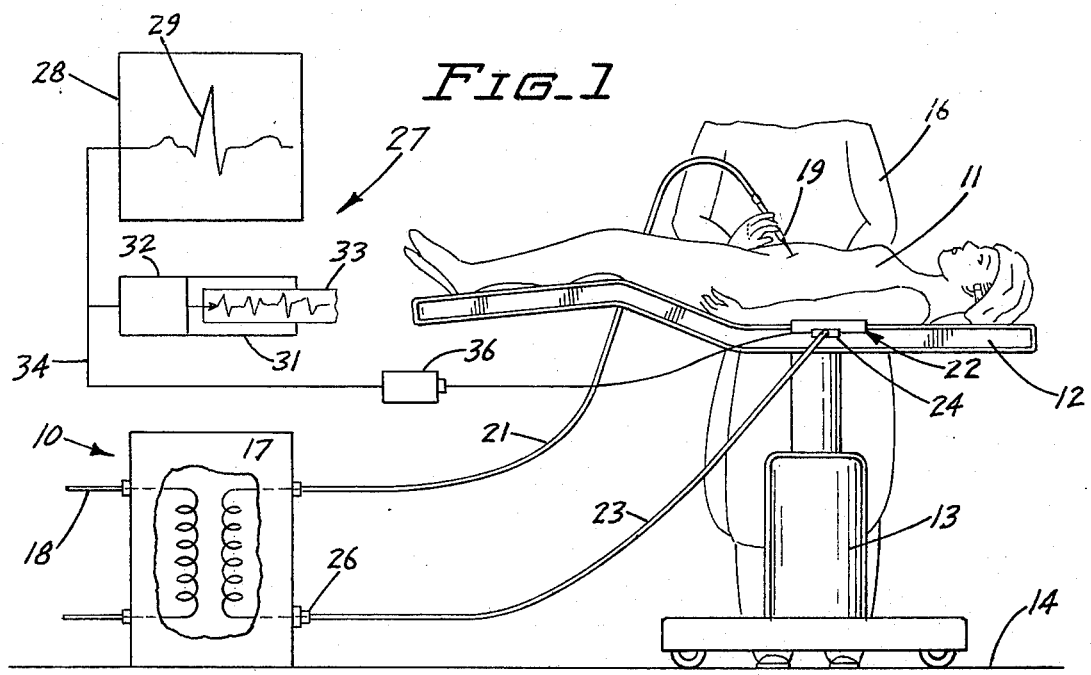
FIG. 1 is a diagrammatic view of an ECG monitoring and electrosurgical operating system of the invention as used with a patient on an operating table.

Referring to FIG. 1, there is shown an electrosurgical unit indicated generally at 10 in an operating environment or theater on a patient 11. Patient 11 is located in a prone position on an operating table 12. An upright base 13 supports table 12 above floor 14 to locate patient 11 in a convenient position for surgeon 16 and supporting operating personnel.

Figure 2:
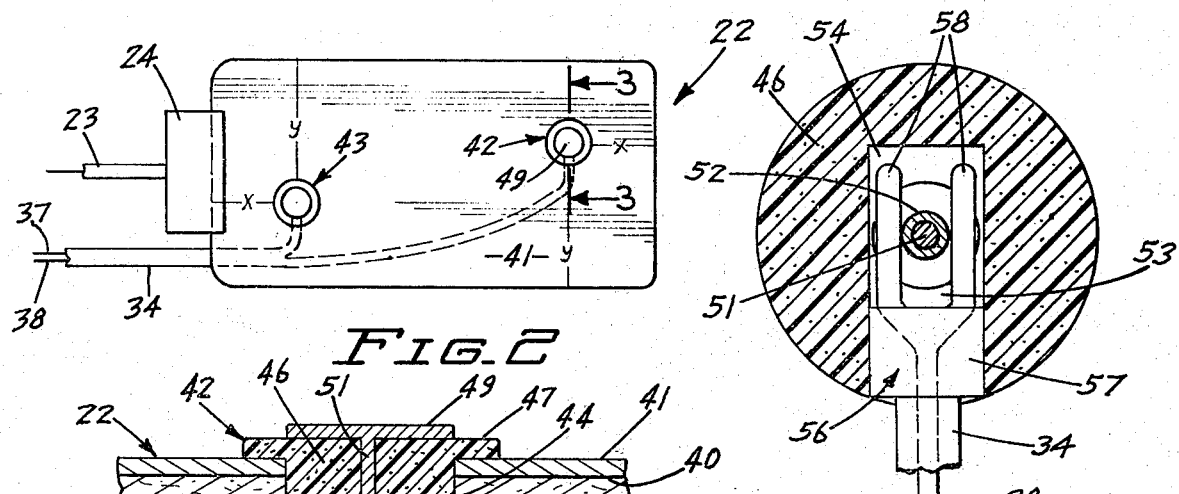
FIG. 2 is an enlarged plan view of the ground electrode and ECG pickup electrode assembly used in the system of FIG. 1.

Electrosurgical unit 10 uses high frequency electric current from a transformer or generator 17 connected to a power supply 18. An active electrode 19 is used by surgeon 16 in the operating procedure. Active electrode 19 is connected to transformer 17 with a cable or line 21. Generator 17 is a radio frequency (RF) source which applies a high density current to the active electrode 19 at a relatively high voltage. The high density current causes localized cutting or coagulating action. A ground plate electrode or indifferent electrode indicated generally at 22 is connected by cable 23 to the generator 17. A releasable clamp 24 connects the cable to the electrdoe 22, as shown in FIG. 2. The opposite end of cable 23 carries a plug 26 connected to the generator 17. Clamp 24 is releasably mounted on one end of electrode 22 and can be clamped, as shown in U.S. Pat. Nos. 3,543,760, 3,624,590, 3,642,008 and 3,842,394.

An ECG monitoring system indicated generally at 27 is used in conjunction with the electrosurgical unit 10 to monitor the patient's heart signals during the electrosurgical operation. ECG monitoring system 27 has an electronic signal viewing screen 28 operable to provide an instantaneous visual heart tracing 29. Tracing 29 is used to provide the surgeon with visual information regarding the rhythm, rate and wave form of the cardiac signals. The physician, when viewing the screen, has an instantaneous and continuous heart signal, allowing assessment of cardiac stress during the electrosurgical procedure and detection of cardiac arrhythmia. A recorder 31 having a stylus drive 32 operates to make a heart tracing on a strip chart 33. An electrically conductive line or cable 34 connects the screen 28 and recorder 31 to the electrodes used to sense the bioelectric heart signals hereinafter described.

Cable 34 is shielded to minimize interference from extraneous electrical signals. A filter 36 is interposed in line 34 to filter noise signals that will interfere with the cardiac signals.

The ground electrode 22 has a generally rectangular flexible cardboard base 39. One side of the base is covered with an electrically conductive skin or conductor 41. The surface area of skin 41 is of a size to be in surface contact with the body of the patient and thereby minimize accidental burning of the patient. The base 39 can be made of cardboard, plastic, paper or like electrically insulative materials. The skin 41 is preferably of electrically conductive metal, as aluminum foil, tin, silver, copper, or like metals. Electrically conductive inks and cloths, as silver and Nylon, can be used as the electrical conductor 41 with base 39. Skin 41 can also be deposited on the base or substrate by a metal deposition method, as disclosed in U.S. Pat. No. 3,485,643.

Electrode 22 has a rectangular shape with four corners having round configurations to eliminate any sharp points or edges that may injure tha patient or technician using the electrode. The outside edges and ends of the skin 41 are turned down adjacent to the sides of the base to eliminate sharp edges that can cut the patient or technicians.

Figure 3:
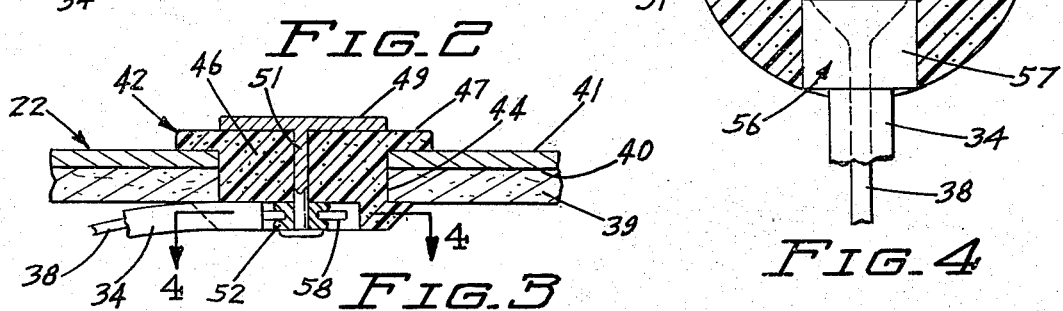
FIG. 3 is an enlarged sectional view taken along the line 3—3 of FIG. 2.

The skin 41, in the form of metal foil, can be applied in a process which utilizes a moving base 39. An adhesive layer 40, as shown in FIG. 3, is initially applied to the base 39. A continuous strip of metal foil is laid down on the base and pressed into engagement with the top side of the base. The sheet comprising the base and skin is set into a die cutter which stamps out the plate electrode. During the die cutting process, separate holes 44 are stamped into the electrode to accommodate the bioelectric pickup electrodes indicated generally at 42 and 43. The process of making the electrode accurately locates the skin on the base in an efficient and economical manner. The entire inside surface of skin 41 is secured to base 39 with the adhesive 40 without wrinkling or tearing the metal foil of the skin 41.

Preferably, electrode 22 has a width of 20 cm. and a length of 40 cm. The surface area of the electrode is about 800 square cm. Other shapes and sizes can also be used.

The biolelectric pickup electrodes 42 and 43 are identical in construction and are located in opposite diagonal corners of the electrode 22. The following description is limited to bioelectric pickup electrode 42.

Pickup electrode 42 is located in hole 44 in electrode 22. Electrode 42 has an electrically insulative body 46 extended through hole 44. An outwardly directed top flange 47 extends over the skin 41. A similar lower flange 48 extends over base 39 and thereby holds body 46 in assembled relation with electrode 22. A flat, electrically conductive member or film 49 is mounted on top of the body 46. A stem 51 is connected to the bottom of member 49 and extends through body 46. A connector 52 is mounted on the lower end of stem 51 and thereby holds member 49 in assembled relation with body 46. Connector 52 has an annular slot or groove 53 forming the female part of the electrical connection with the line 38 of cable 34. Connector 52 is located in a recess or space 54 in the bottom of body 46.

Figure 4:
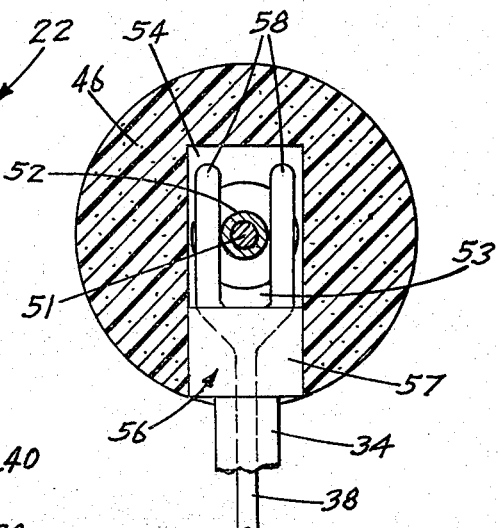
FIG. 4 is an enlarged sectional view taken along the line 4—4 of FIG. 3.

As shown in FIG. 4, the end of cable 34 has a plug 56 adapted to be releasably connected to connector 52. Plug 56 has a body 57 which fits into the open end of space 54. A pair of forwardly directed spaced fingers 58 extend from plug 56 and engage opposite sides of the connector to thereby make an electrical connection between cable 34 and the connector 52.

Body 46 can be of a resilient foam-like material whereby body 46 will bias the electrically conductive member 49 into engagement with the skin of a patient. The flange 47 surrounding the member 49 electrically insulates member 49 from skin 41 of the ground plate.

The bioelectric pickup electrode 42 is located a distance indicated as X from the end of the electrode and a distance indicated as Y from one side of the electrode. Bioelectric pickup electrode 43 is located a distance indicated as X from the opposite end of the electrode and a distance indicated as Y from the opposite edge of the electrode. An equal amount of electrically conductive skin 41 surrounds the electrodes 42 and 43 so that the potential difference of the heart signals sensed by electrodes 42 and 43 is not affected by the electrosurgical signals that are sensed by the ground electrode 22.

Figure 5:
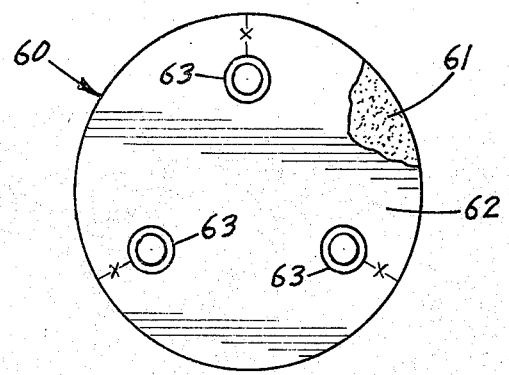
FIG. 5 is a plan view of a first modification of the ground electrode and ECG pickup electrode assembly useable with the cautery and monitoring system of FIG. 1.

A modification of the ground electrode and ECG pickup electrode apparatus is shown in FIG. 5. The electrode apparatus has a round shape and comprises a base 61. A first electrically conductive means or skin 62 is secured to one side of the base. Suitable adhesives or bonding materials can be used to secure the conductor to the base. The base 61 is a flat, electrically insulative material, such as cardboard, plastic, paper or the like. The electrical conductor 62 can be made of the same material as the electrically conductive skin 41 of electrode 22. Three spaced bioelectric cardiac pickup electrodes 63 are mounted on the base 61. The electrodes 63 are equally spaced from each other so that the same amount of surface area of the electrical conductor 62 surrounds each pickup electrode 63. The pickup electrode 63 includes an electrically insulative member mounted on the base 61. The pickup electrodes 63 are identical to the structure shown in FIG. 3. Each pickup electrode is spaced from the outer peripheral edge of the electrode 60 by the same distance X.

Figure 6:
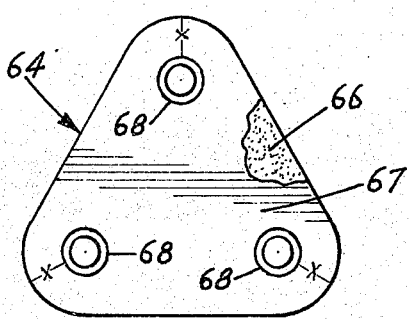
FIG. 6 is a second modification of a ground electrode and ECG pickup electrode assembly useable in the cautery and ECG monitoring system of FIG. 1.

Referring to FIG. 6, there is shown a second modification of the electrode apparatus indicated generally at 64. This electrode apparatus is useful with the cautery and ECG monitoring system as shown in FIG. 1 in lieu of electrode 22. Electrode apparatus 64 has a generally triangular configuration with rounded apexes. Electrode apparatus 64 has a base 66 carrying an electrically conductive means or skin 67. Base 66 can be made of the same material as the base 61 and the conductor skin 67 can be made of the same material as skin 62 of FIG. 5. A plurality of bioelectric pickup electrodes 68 are mounted on base 66. Pickup electrodes 68 are spaced from each other by equal distance and are equally spaced by distance X from the apexes of electrode apparatus 64. Bioelectric pickup electrodes 68 are mounted on base 66 in the same manner as the structure shown in FIG. 2. An electrically insulative member is used to isolate each bioelectric pickup electrode from the ground electrode conductor skin 67.

While there has been shown and described a preferred embodiment of the invention and ground electrode and bioelectric pickup electrode combination, it is understood that changes in the shape, materials, and size may be made by those skilled in the art without departing from the invention. For example, the number of bioelectric pickup electrodes can be increased and all the electrodes equally spaced from each other so that substantially the same amount of electrically conductive skin surrounds each electrode.

The embodiments of the invention in which an exclusive property or privilege is claimed are defined as follows:

1. An electrode for use with an electrosurgical apparatus to ground a patient and used with an ECG monitoring instrument to sense bioelectric cardiac signals of a patient comprising: an electrically insulative sheet member having a surface, first electrical conductor means attached to said surface providing a ground electrode adapted to be located in surface contact with the patient, said first electrical conductor means being connectable to the electrosurgical apparatus, second electrical conductor means providing a plurality of bioelectric signal pickup electrodes, means for electrically connectng each pickup electrode with the ECG monitoring instrument, and electrically insulative means mounting each pickup electrode on said surface of the sheet member and separating each pickup electrode from the first electrical conductor means, said pickup electrodes being equally spaced from each other, said first electrical conductor means completely surrounding said pickup electrodes so that the same amount of surface area of the first electrical conductor means completely surrounds each pickup electrode.

2. The electrode of claim 1 wherein: said pickup electrodes comprise two pickup electrodes.

3. The electrode of claim 1 wherein: said pickup electrodes comprise three pickup electrodes.

4. The electrode of claim 1 wherein: the sheet member is a flat, flexible and electrically insulative member.

5. The electrode of claim 4 wherein: the first electrical conductor means is a metal skin attached to the sheet member.

6. The electrode of claim 5 wherein: the metal skin is aluminum.

7. The electrode of claim 1 wherein: the sheet member has holes accommodating the electrically insulative means to mount the electrically insulative means on the sheet member.

8. The electrode of claim 1 wherein: the bioelectric pickup electrodes are flat electrical conductors mounted on the electrically insulative means.

9. The electrode of claim 1 wherein: the electrically insulative means are resilient members operable to yieldably urge the pickup electrodes in the direction for engagement with the body of a patient.

10. The electrode of claim 1 wherein: the sheet member has a rectangular shape.

11. The electrode of claim 1 wherein: the sheet member has a circular shape.

12. The electrode of claim 1 wherein: the sheet member has a triangular shape.

13. An apparatus for use with an electrosurgical unit to ground a patient and for use with an ECG monitoring instrument to sense bioelectric cardiac signals of a patient comprising: electrode means having first electrical conductor means adapted to be located in surface contact with a patient to ground the patient, second electrical conductor means providing a plurality of bioelectric signal pickup electrodes and electrically insulative means separating the pickup electrodes from the first electrical conductor means, said pickup electrodes being equally spaced from each other other, said first electrical conductor means completely surrounding said pickup electrodes so that the same amount of surface area of the first electrical conductor means completely surrounds each pickup electrode, first line means for electrically connecting the first electrical conductor means with the electrosurgical unit; and second line means for electrically connecting each pickup electrode with the ECG monitoring instrument.

14. The apparatus of claim 13 including: releasable clamp means connecting the first line means to the first electrical conductor means.

15. The apparatus of claim 13 including: plug means to connect the first line means to the electrosurgical unit.

16. The apparatus of claim 13 including: releasable connector means connecting the second line means to the pickup electrodes.

17. The apparatus of claim 13 including: means to connect the second line means to the ECG monitoring instrument.

18. The apparatus of claim 13 wherein: said pickup electrodes comprise two pickup electrodes.

19. The apparatus of claim 13 wherein: said pickup electrodes comprise three pickup electrodes.

20. The apparatus of claim 13 wherein: the electrode means has a flat, flexible and electrically insulative sheet member, said first electrical conductor means being mounted to the sheet member.

21. The apparatus of claim 20 wherein: the first electrical conductor means is a metal skin attached to the sheet member.

22. The apparatus of claim 21 wherein: the metal skin is aluminum.

23. The apparatus of claim 13 wherein: the electrode means includes an electrically insulative sheet member having holes accommodating the electrically insulative means to mount the electrically insulative means on the sheet member.

24. The apparatus of claim 13 wherein: the bioelectric pickup electrodes are generally flat electrical conductors mounted on the electrically insulative means.

25. The apparatus of claim 13 wherein: the electrically insulative means are resilient members operable to yieldably urge the pickup electrodes in the direction for engagement with the body of a patient.

26. An electrode for use with an electrosurgical apparatus to ground a patient and for use with an ECG monitoring instrument to sense bioelectric cardiac signals of a patient comprising: electrode means having first electrical conductor means adapted to be located in surface contact with a patient to ground the patient, said first conductor means being connectable to the electrosurgical apparatus, second electrical conductor means providing a plurality of bioelectric signal pickup electrodes, means for electrically connecting each pickup electrode with the ECG monitoring instrument, and electrically insulative means separating the pickup electrodes from each other and from the first electrical conductor means, said pickup electrodes being equally spaced from each other and spaced relative to the first electrical conductor means, said first electrical conductor means located completely around said pickup electrodes so that the same amount of surface area of the first electrical conductor means is located completely around each pickup electrode whereby said electrode means can concurrently ground the patient during operation of the electrosurgical apparatus and sense the bioelectric cardiac signals so that the signals can be monitored by the ECG monitoring instrument.

27. The electrode of claim 26 wherein: said pickup electrodes comprise two pickup electrodes.

28. The electrode of claim 26 wherein: said pickup electrodes comprise three pickup electrodes.

29. The electrode of claim 26 wherein: the electrode means has a flat, flexible and electrically insulative sheet member, said first electrical conductor means being mounted on one side of the sheet member.

30. The electrode of claim 29 wherein: the first electrical conductor means is a metal skin attached to the sheet member.

31. The electrode of claim 30 wherein: the metal skin is aluminimum.

32. The electrode of claim 26 wherein: the electrode means includes an electrically insulative sheet member having holes accommodating the electrically insulative means to mount the electrically insulative means on the sheet member.

33. The electrode of claim 26 wherein: the bioelectric pickup electrodes are generally flat electrical conductors mounted on the electrically insulative means.

34. The electrode of claim 26 wherein: the electrically insulative means include resilient members operable to yieldably urge the pickup electrodes in the direction for engagement with the body of a patient.

* * * * *